(12) United States Patent
Magnin et al.

(10) Patent No.: US 10,512,446 B2
(45) Date of Patent: *Dec. 24, 2019

(54) METHOD AND SYSTEM FOR IMAGING, DIAGNOSING, AND/OR TREATING AN AREA OF INTEREST IN A PATIENT'S BODY

(71) Applicant: VOLCANO CORPORATION, San Diego, CA (US)

(72) Inventors: Paul A. Magnin, Andover, MA (US); Russell W. Bowden, Tyngsboro, MA (US); John W. Goodnow, Arlington, MA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/033,663

(22) Filed: Jul. 12, 2018

(65) Prior Publication Data
US 2018/0317880 A1    Nov. 8, 2018

Related U.S. Application Data

(60) Continuation of application No. 13/935,084, filed on Jul. 3, 2013, now Pat. No. 10,039,522, which is a (Continued)

(51) Int. Cl.
*A61M 25/01* (2006.01)
*A61B 8/12* (2006.01)
(Continued)

(52) U.S. Cl.
CPC ............... *A61B 8/12* (2013.01); *A61B 8/445* (2013.01); *A61B 8/4461* (2013.01);
(Continued)

(58) Field of Classification Search
CPC ...................... A61M 2505/0183; A61B 8/4461
See application file for complete search history.

(56) References Cited

U.S. PATENT DOCUMENTS 3,542,014 A    11/1970 Peronneau
3,779,234 A    12/1973 Eggleton et al.
(Continued)

OTHER PUBLICATIONS

Evans et al, "Arterial Imaging with a New Forward-Viewing Intravascular Ultrasound Catheter, I, Initial Studies," Circulation, vol. 89, No. 2, DD 712-717, Feb. 1994.
(Continued)

*Primary Examiner* — Laura A Bouchelle

(57) ABSTRACT

A method and system for imaging, diagnosing, and/or treating an area of interest in a patient's body is provided. More particularly, a manually steered "rapid exchange" type catheter for a system for imaging, diagnosing, and/or an area of interest in a patient's body is provided. The catheter comprises a catheter body configured to be introduced to an area of interest in a patient's body, a device for imaging, diagnosing, and/or treating the area of interest contained within the catheter body, and a manual steering device attached to the imaging, diagnosing, and/or treating device to allow an operator to manually steer the imaging, diagnosing, and/or treating device, wherein the catheter is configured to be mounted on a commercially available guidewire.

10 Claims, 7 Drawing Sheets

Related U.S. Application Data continuation of application No. 12/861,396, filed on Aug. 23, 2010, now Pat. No. 8,491,567, which is a division of application No. 11/392,557, filed on Mar. 30, 2006, now Pat. No. 7,785,286.

(51) Int. Cl.
| | |
|---|---|
| *A61B 8/00* | (2006.01) |
| *A61B 18/14* | (2006.01) |
| *A61B 17/00* | (2006.01) |
| *A61M 25/00* | (2006.01) |
| *A61B 90/00* | (2016.01) |

(52) U.S. Cl.
CPC ..... *A61M 25/0133* (2013.01); *A61B 18/1492* (2013.01); *A61B 2017/00336* (2013.01); *A61B 2090/3782* (2016.02); *A61M 25/0082* (2013.01); *A61M 2025/0183* (2013.01)

(56) References Cited

U.S. PATENT DOCUMENTS

| | | |
|---|---|---|
| 3,817,089 A | 6/1974 | Eggleton et al. |
| 3,827,115 A | 8/1974 | Born |
| 3,938,502 A | 2/1976 | Born |
| 4,316,390 A | 2/1982 | Kretz |
| 4,391,282 A | 7/1983 | Ando et al. |
| 4,408,612 A | 10/1983 | Utsugi |
| 4,489,728 A | 12/1984 | Matsuo et al. |
| 4,587,972 A | 5/1986 | Morantte, Jr. |
| 4,794,931 A | 1/1989 | Yock |
| 4,805,155 A | 2/1989 | Shiraishi et al. |
| 4,841,977 A | 6/1989 | Griffith et al. |
| 4,899,757 A | 2/1990 | Pope, Jr. et al. |
| 4,911,170 A | 3/1990 | Thomas, III et al. |
| 4,917,097 A | 4/1990 | Proudian et al. |
| 4,951,677 A | 8/1990 | Crowley et al. |
| 5,000,185 A | 3/1991 | Yock |
| 5,024,234 A | 6/1991 | Leary et al. |
| 5,054,492 A | 10/1991 | Scribner et al. |
| 5,115,814 A | 5/1992 | Griffith et al. |
| 5,127,409 A | 7/1992 | Daigle |
| 5,131,397 A | 7/1992 | Crowley |
| 5,176,141 A | 1/1993 | Born et al. |
| 5,186,177 A | 2/1993 | O'Donnell et al. |
| 5,203,338 A | 4/1993 | Jang |
| 5,240,003 A | 8/1993 | Lancee et al. |
| 5,243,988 A | 9/1993 | Sieben et al. |
| 5,271,400 A | 12/1993 | Dumoulin et al. |
| 5,271,402 A | 12/1993 | Yeung et al. |
| 5,284,148 A | 2/1994 | Dias et al. |
| 5,313,949 A | 5/1994 | Yock |
| 5,321,501 A | 6/1994 | Swanson et al. |
| 5,345,940 A | 9/1994 | Seward et al. |
| 5,353,798 A | 10/1994 | Sieben |
| 5,361,768 A | 11/1994 | Webler et al. |
| 5,368,035 A | 11/1994 | Hamm et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,685 A | 1/1995 | Kazi et al. |
| 5,379,772 A | 1/1995 | Imran |
| 5,429,136 A * | 7/1995 | Milo ........................ A61B 8/12 600/439 |
| 5,439,000 A | 8/1995 | Gunderson et al. |
| 5,469,853 A | 11/1995 | Law et al. |
| 5,485,845 A | 1/1996 | Verdonk et al. |
| 5,588,432 A | 12/1996 | Crowley |
| 5,594,842 A | 1/1997 | Kaufman et al. |
| 5,606,454 A | 2/1997 | Williams et al. |
| 5,651,366 A | 7/1997 | Liang et al. |
| 5,699,806 A | 12/1997 | Webb et al. |
| 5,921,934 A | 7/1999 | Teo |
| 6,029,671 A | 2/2000 | Stevens et al. |
| 6,066,096 A | 5/2000 | Smith et al. |
| 6,095,981 A | 8/2000 | McGahan |
| 6,120,455 A | 9/2000 | Teo |
| 6,267,727 B1 | 7/2001 | Teo |
| 6,445,939 B1 | 9/2002 | Swanson et al. |
| 6,450,964 B1 | 9/2002 | Webler |
| 6,457,365 B1 | 10/2002 | Stephens et al. |
| 6,780,157 B2 | 8/2004 | Stephens et al. |
| 6,860,855 B2 | 3/2005 | Shelby et al. |
| 6,863,676 B2 | 3/2005 | Lee et al. |
| 6,960,172 B2 | 11/2005 | McGuckin, Jr. et al. |
| 7,022,082 B2 | 4/2006 | Sonek et al. |
| 7,025,765 B2 | 4/2006 | Balbierz et al. |
| 7,612,773 B2 | 11/2009 | Magnin et al. |
| 7,785,286 B2 * | 8/2010 | Magnin .................... A61B 8/12 604/22 |
| 10,039,522 B2 * | 8/2018 | Magnin .................... A61B 8/12 |
| 2002/0032437 A1 | 3/2002 | Andrews et al. |
| 2002/0183826 A1 | 12/2002 | Dorn et al. |
| 2003/0125757 A1 | 7/2003 | Patel et al. |
| 2003/0199747 A1 * | 10/2003 | Michlitsch ............... A61B 5/01 600/407 |
| 2004/0113909 A1 | 6/2004 | Fenney et al. |
| 2005/0107688 A1 | 5/2005 | Strommer |
| 2005/0128730 A1 | 6/2005 | Shindoh |
| 2007/0106155 A1 | 5/2007 | Goodnow |
| 2008/0287801 A1 | 11/2008 | Magnin et al. |

OTHER PUBLICATIONS

Ng et al., "Arterial Imaging with a New Forward-Viewing Intravascular Ultrasound Catheter, II, Three-Dimensional Reconstruction and Display of Data," Circulation, vol. 89, No. 2, pp. 718-723, Feb. 1994.

Liang, D.H., "A Forward-Viewing Intravascular Ultrasound Catheter Suitable for Intracoronary Use," Biomedical Instrumentation & Technoloav, Jan./Feb. 1997. pp. 45-53.

Von Birgelen C., et al., "Preintervention Lesion Remodeling Affects Operative Mechanisms of Balloon Optimized Directional Coronary Atherectomy Procedures: a volumetric study with three dimensional intravascular ultrasound," Heart 2000, vol. 83, DD. 192-197.

Wolfram Research, "Mathworld: Rodrigues' Rotation Formula," httD://mathworld.wolfram.com/RodriguesRotationFormula.html.

Catmull, E., "A Subdivision Algorithm for Computer Display of Curved Surfaces," Ph.D. Thesis, Report UTEC-CSc-74-133, Computer Science Department, University of Utah, Salt Lake City, UT, Dec. 1974. Also in "Computer Display of Curved Surfaces," Proc. IEEE Conf. on Computer Graphics, Pattern Recognition and Data Structures, May 1975.

Blinn, J.F., and M.E. Newell, Texture and Reflection in Computer Generated Images, Communications of the ACM, 19(10), Oct. 1976, pp. 542-547.

Heckbert, P.S., "Survey of Texture Mapping," IEEE Computer Graphics and Applications, 6(11), Nov. 1986, pp. 56-67.

Feldman, Mark, "The PC Game Programmer's Encyclopedia: Texture Mapping," http://www.cieocities.com/SiliconValley/2151/tmap.html.

Research Laboratory of Electronics at MIT Optical Devices—Laser Medicine and Medical Imaging Group, Progress Report 143, Chapter 11.

Research Laboratory of Electronics at MIT—Photonic Materials, Devices and Systems—Laser Medicine and Medical Imaging Group, Progress Report 144, Chapter 27.

International Search Report dated Dec. 28, 2007.

Slager et al., "Vaporization of Atherosclerotic Plaque by Spark Erosion," JACC, Jun. 1985, 5:00. 1382-1386-6.

Slager, et al., "Spark Erosion and Its Combination with Sensing Devices for Ablation of Vascular Lesions," Chapter 13, in John H.K. Vogel and Spencer B. Kin, III, Interventional Cardiology: Future Directions, The C.V. Mosby Company, St. Louis, 1989, DD. 163-169. Presented Sep. 26, 1987 Santa Barbara.

Born et al., "Intra-Arterial Ultrasonic Imaging for Recanalization by Spark Erosion," Ultrasound in Med & Biol., vol. 14, No. 4, DD. 257-261, 1988.

(56) References Cited

OTHER PUBLICATIONS

Born et al., "Early and Recent Interluminal Ultrasound Devices," International Journal of Cardiac Imaging 4:79-88, 1989, 1989 Kluwer Academic Publishers, Printed in the Netherlands.

Harm ten Hoff et al., "Imaging artifacts in mechanically driven ultrasound catheters" 1989, vol. 4, pp. 195-199, International Journal of Cardiac Imaging.

Kimura et al., "Can Intravascular Ultrasound Yield Accurate Measurements of Vascular Anatomy? Documentation of the Critical Importance of Uniform Rotational Velocity" 1994, vol. 1A(484) p. 173A, JACC.

Slager et al., "Removal of Cardiovascular Obstructions by Spark Erosion," public presentation of dissertation, Dec. 17, 1997 at 3:45 PM, later printed in "Spark Erosion Under Ultrasound Guidance," Ch. 8, pp. 81-90. ICG Printing Dordrecht.

\* cited by examiner

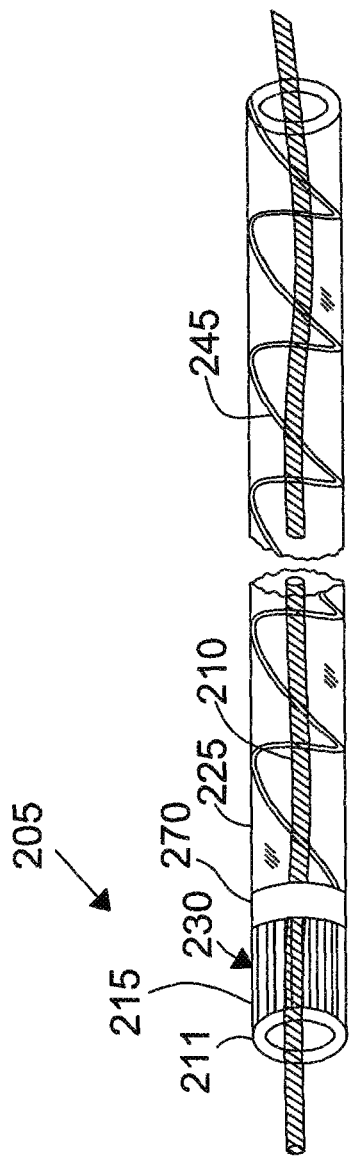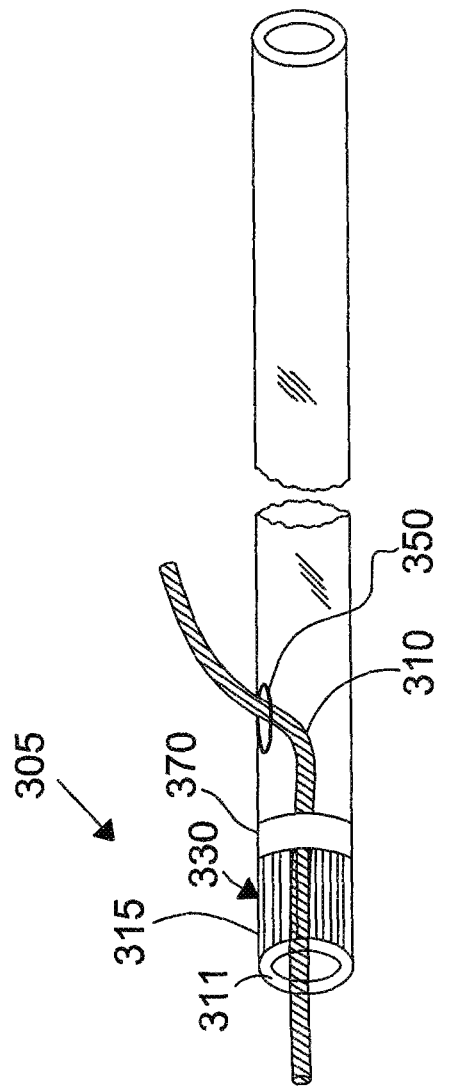

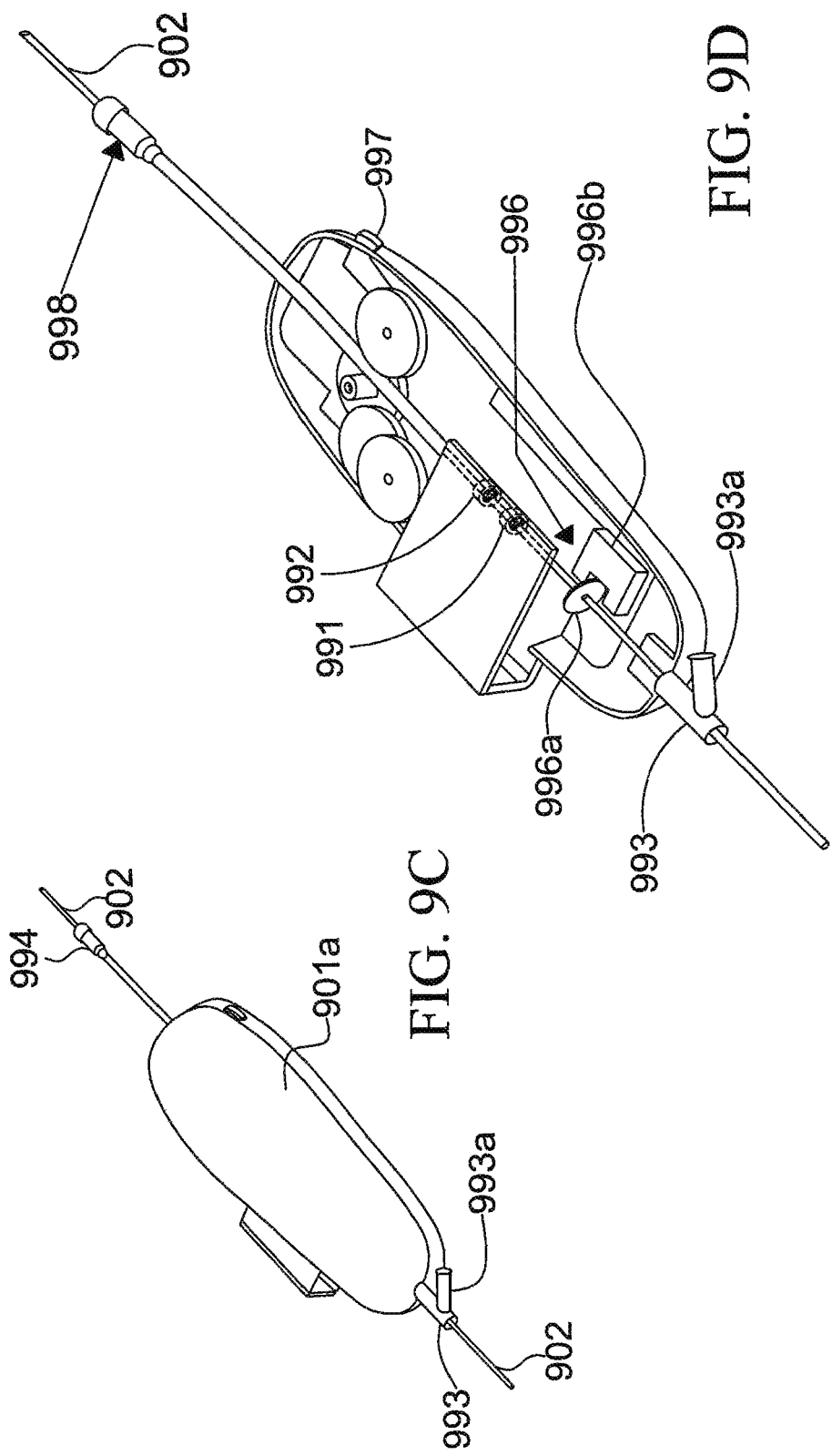

METHOD AND SYSTEM FOR IMAGING, DIAGNOSING, AND/OR TREATING AN AREA OF INTEREST IN A PATIENT'S BODY

This application is a continuation of U.S. application Ser. No. 13/935,084, filed Jul. 13, 2013, which is a continuation of U.S. application Ser. No. 12/861,396, filed Aug. 23, 2010, now U.S. Pat. No. 8,491,567, which is a divisional of U.S. application Ser. No. 11/392,557, filed Mar. 30, 2006, now U.S. Pat. No. 7,785,286.

BACKGROUND OF THE INVENTION

1. Field of the Invention

The invention relates to a method and system for imaging, diagnosing, and/or treating an area of interest in a patient's body.

2. Background of the Related Art

The use of less invasive, catheter-based, intravascular techniques has been developed over several decades and may be considered the preferred mode of treatment for those patients amenable to such treatment. Typically, intravascular procedures, such as angioplasty, atherectomy, and stenting, are preceded by a diagnostic procedure, such as angiography and in some cases IntraVascular UltraSonic (IVUS) imaging.

IVUS imaging can frequently provide additional diagnostic information over what is readily obtained using a fluoroscope and radio-opaque dyes as in angiography. This stems from the fact that geometric measurements are based on cross-sectional images not "shadow grams" as in single plane angiography and by virtue of the high contrast nature of the interaction of sound with tissue as opposed to the interaction of x-rays with tissues. Further, the angiogram requires the use of x-ray contrast agents that opacify the blood pool and therefore are not intended to examine the tissue in the vessel wall, but rather the path of the blood pool itself.

With almost all modern interventional catheter procedures, an interventionalist or operator first places a guidewire into a target anatomy or site, such as a vessel(s), artery, or other body cavity of diagnostic or therapeutic interest. The guidewire is used to navigate the target anatomy in the patient's body prior to the diagnostic or therapeutic catheter being inserted.

The placement of the guidewire is frequently the most difficult and time consuming part of the entire procedure. Consequently, once the guidewire has been advanced into the target anatomy, the interventionalist or operator does not want to lose the position of the distal end of the guidewire.

After the guidewire is in place, various diagnostic and therapeutic catheters, such as balloon catheters, stent deployment catheters, atherectomy catheters, IVUS catheters, and thrombectomy catheters, are "loaded" over the guidewire. The guidewire, so placed, serves as a rail along which catheters can be advanced directly to, and withdrawn from, the target site.

There are two basic categories of catheters that are used in conjunction with these guidewires. The first category of catheters is referred to as "Over-The-Wire" (OTW) devices. Catheters in the first category have a lumen that extends inside the entire length of the catheter into which a guidewire can be inserted. The second category of catheters is referred to as "RX" or "rapid exchange" (RX) catheters. In these catheters, the guidewire only enters into the catheter body near its distal end, instead of entering at the proximal-most end, and extends inside the catheter body to the distal most end of the catheter where it exits.

There are advantages and disadvantages to both designs. The OTW catheters allow easy exchange of guidewires should additional catheter support, from a stiffer guidewire, or a change in the shape or stiffness of the guidewire tip be necessary. The RX catheters allow the operator to more rapidly change from one catheter to another while leaving the guidewire in place, thereby preserving the placement of the guidewire distal tip, which may have been difficult to achieve. Although "standard" length (typically ~190 cm) guidewires usually have a proximal extension capability built in (extending the overall length to ~300 cm), the use of these accessories is cumbersome and can require two sterile operators.

Typically, ~190 cm guidewires are required to span a vessel from the most distal anatomy that the interventionalist or operator wishes to treat to the point where the guide catheter, enters the patient's body. The entry point may be located, for example, at the femoral artery in a patient's groin, or on occasion, the radial artery in a patient's arm. If the catheter being loaded over the guidewire is an OTW catheter, the guidewire must be long enough so that the entire length of the OTW catheter can be slid over the proximal end of the guidewire and yet there remain some length of the guidewire exposed where it enters the patient's body. That is, the guidewire for an OTW catheter must be approximately twice as long as one that is to be used only with RX catheters, because it must simultaneously accommodate both the length inside the patient's body and the length of the OTW catheter. Further, the "threading" of the OTW catheter over the distal or proximal end of the guidewire is time consuming, and the added length of the guidewire can be cumbersome to handle while maintaining sterility.

Since the RX design catheters typically have the guidewire running inside them for only the most distal ~1 cm to ~30 cm, the guidewire employed need only have a little more than the required ~1 cm to ~30 cm after it exits the patient's body. While the loading of an ~140 cm OTW catheter over an ~280 cm to ~300 cm guidewire is time consuming and tedious, loading the distal ~10 cm of an RX catheter over a shorter guidewire is easily done.

However, OTW catheters tend to track the path of the guidewire more reliably than RX catheters. That is, the guidewire, acting as a rail, prevents buckling of the catheter shaft when it is pushed forward from its proximal end over the guidewire. RX catheters can, however, given a sufficiently wide target site, such as a sufficiently wide artery, and a sufficiently tortuous guidewire path, buckle as they are advanced along the guidewire by pushing on the proximal end of the catheter. In addition, when an RX catheter is withdrawn from a patient, the RX portion can pull on the guidewire and cause the guidewire to buckle near the point that it exits the proximal end of the RX channel.

There are advantages to both designs. However, when the path of the target anatomy, such as a vessel, that is to be imaged is not too tortuous and the location of the target imaging site is not too difficult to reach, the mono-rail or RX catheters are preferred.

Recently catheters and systems have been developed to visualize and quantify the anatomy of vascular occlusions by using IVUS imaging. IVUS techniques are catheter-based and provide real-time cross-sectional images of a target anatomy, such as a vessel lumen, diseased tissue in the vessel, and the vessel wall. An IVUS catheter includes one or more ultrasound transducers at or near the distal tip of the catheter by which images containing cross-sectional information of the vessel under investigation can be obtained. IVUS imaging permits accurate geometric measurements, visualization of the atherosclerotic plaques, and the assessment of various therapies and complications that may result.

Motor driven, mechanically steered IVUS imaging systems typically include an arrangement in which a single transducer near the distal end of the catheter is rotated at high speed (up to about 1800 rpm) to generate a rapid series of ~360-degree ultrasound sweeps. This is exemplified by U.S. Pat. No. 4,794,931 to Yock, which is hereby incorporated by reference. Such speeds result in generation of up to about thirty images per second, effectively presenting a real time cross-sectional image of, for example, a diseased vessel or artery.

The transducer assembly is mounted on the end of a drive shaft that is connected to a motor drive at the proximal end of the catheter. Incorporated into the motor drive, or in some cases separate from the motor drive, is an angle encoder that records the angular position of the transducer assembly. The rotating transducer assembly is housed in a sheath that protects the vessel or artery from the rapidly spinning drive shaft. The IVUS imaging catheter is advanced to the region of interest using the guidewire RX technique to provide real-time cross-sectional images of the lumen and the vessel or arterial wall at the desired target site. The presence of a mechanically spinning imaging core in the center of the IVUS catheter prevents OTW versions of motor driven, mechanically steered IVUS catheters.

There is, however, a commercially available, electronically steered IVUS catheter that does not contain a central spinning imaging core that is amenable to either OTW designs or RX designs. Such a catheter and imaging system is disclosed in U.S. Pat. No. 4,917,097 to Proudian, which is hereby incorporated by reference. The electronically steered IVUS catheters have a ring of ultrasonic transducers located at the distal tip of the catheters. Tiny electronic multiplexers located just proximal to the ultrasonic transducers are used to select a subset of the ultrasonic transducers. By selecting different sets of adjacent elements, the ultrasonic beam can be electronically rotated in practically any radial direction around the catheter.

U.S. patent application Ser. No. 11/053,141 (hereinafter the "'141 application"), which is hereby incorporated by reference, teaches a novel combined therapy and IVUS catheter that is neither electronically steered nor attached to an electric motor and spinning rapidly as in conventional commercially available products. The '141 application covers a manually rotated, OTW IVUS system whereby the operator sweeps out a complete image of, for example, a vessel or a sector of a vessel when needed by simply rotating the catheter with his or her hand. There are many advantages to such an approach; however, the apparatus as taught in the '141 application, due in part to its combined role in therapy, is not amenable to a rapid exchange design. The catheter described in the '141 application can, with the removal of the RF ablation antenna, be employed as a purely diagnostic device in a fashion analogous to all other commercially available IVUS devices.

In the '141 application, the entire catheter is rotated in order to sweep out an image, and there is no obvious way to make this type of device into an RX catheter. That is, because in an imaging application the entire shaft of the catheter is rotated frequently and if the guidewire were to enter the catheter body say ~1 cm to ~3 cm from the distal end of the catheter as in an IVUS RX design, the interventionalist or operator would be required to torque both the catheter body and the external length of the guidewire in order to make an image. Rotating the guidewire and the IVUS catheter frequently to make IVUS images would potentially damage the vessel wall and cause geometric distortions in the resulting image due to the increased wind-up and backlash at the distal end of the catheter.

In order to provide for the maximum utility of a manually steered IVUS system, there is a need for both an OTW version and a RX version of catheter depending on the particular application.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

The invention is directed to a method and system for imaging, diagnosing, and/or treating an area of interest in a patient's body.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIGS. 3A and 3B are side views of electronically steered prior art IVUS catheters, an OTW design shown in FIG. 3A and a RX design shown in FIG. 3B;

FIG. 9C is a perspective view of the handle rotation mechanism of FIG. 9A, showing an upper housing portion in place;

FIG. 9D is a perspective view of the handle rotation mechanism of FIG. 9A, showing an angle encoder.

DETAILED DESCRIPTION OF PREFERRED EMBODIMENTS

The present invention is discussed below using an IVUS system as an example. However, the systems, catheters, and methods discussed herein may be utilized with and for any appropriate system, catheter, and/or method for imaging, diagnosing, and/or treating an area of interest on or in a patient's body. Further, the term patient is intended to refer to any type of patient, human or animal.

Figure 1:
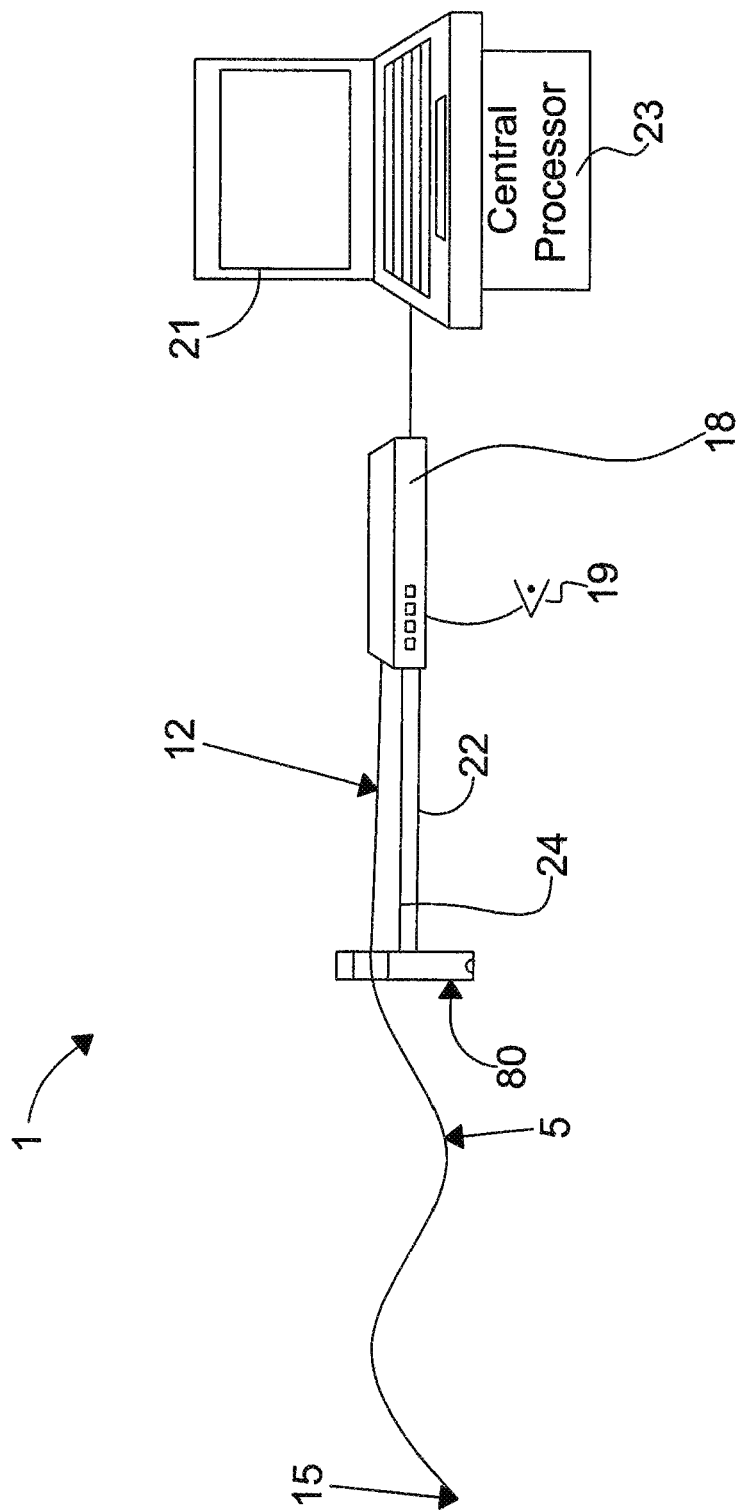
FIG. 1 is a schematic diagram of an IVUS imaging system.

FIG. 1 is a schematic diagram of an IVUS imaging system. The system 1 includes a catheter 5, having proximal and distal ends 12, 15. The distal end or tip 15 is adapted to be inserted into a patient and is constructed to be navigable through the patient's vasculature to advance the distal end 15 to an area or site of interest. The distal tip 15 of the catheter 5 carries an ultrasound transducer (not shown). Further, the distal end 15 may also carry an ablation electrode (not shown) adapted to ablate an obstructed portion of a vessel or other body cavity. The proximal end 12 of the catheter 5 is designed to remain outside of the patient where it can be associated with an angle encoder 80 and can be manipulated by an operator, such as an interventionalist or physician.

The system 1 further includes an electronics module 18 that includes circuitry and software for generating signals for operating the system 1 and for receiving and processing signals from resulting ultrasound echoes, as well as for generating an RF ablation signal if an ablation electrode is included in the system. A central processing unit 23 constructs images from the received ultrasound signals and displays the images on a monitor 21. The images are generated on demand and are refreshed in response to operator rotation of the catheter 5. The images may be caused to fade after a predetermined time as a reminder to an operator to refresh the image by rotating the catheter 5. The central processing unit 23 may comprise, for example, a laptop or desktop computer or a dedicated embedded processor. Cables 22, 24 are connected between the angle encoder 80 and the electronics module 18. In this embodiment, the cable 22 carries incremental angle information that is sensed by the angle encoder 80 and cable 24 provides power and ground. Separate cables run from the catheter 5 to the electronics module 18 and carry ultrasound signals and also RF energy if an ablation electrode is included in the system. In an alternate arrangement (not shown), transducer and RF cables from the catheter 5 may plug into a connector integrated into the angle encoder 80 and then, after pre-amplifying the ultrasound signals, pass the signals through a second connector on the angle encoder 80 to the electronics module 18. This alternate arrangement allows for a shorter catheter cable and, potentially, reduces environmental noise pick-up.

One feature of this system is that the catheter is rotated and manipulated entirely under manual control of the operator. Similarly, in the case where an ablation electrode is included in the system 1, initiation of an ablation pulse may be determined by the operator independently of any direct connection with the catheter or the system for sensing catheter rotation. It should be understood that reference to "manual" with respect to control over the application of ablation energy includes any arrangement by which the operation, based on judgment as to the proper location of the ablation electrode, initiates the ablation sequence. Thus, "manual" operation may include a variety of arrangements, including, mechanically controlled switches, for example, a foot switch, or a voice-operated control or other means by which the operator can trigger an ablation cycle, for example, by manipulation of pedal 19.

Figure 2:
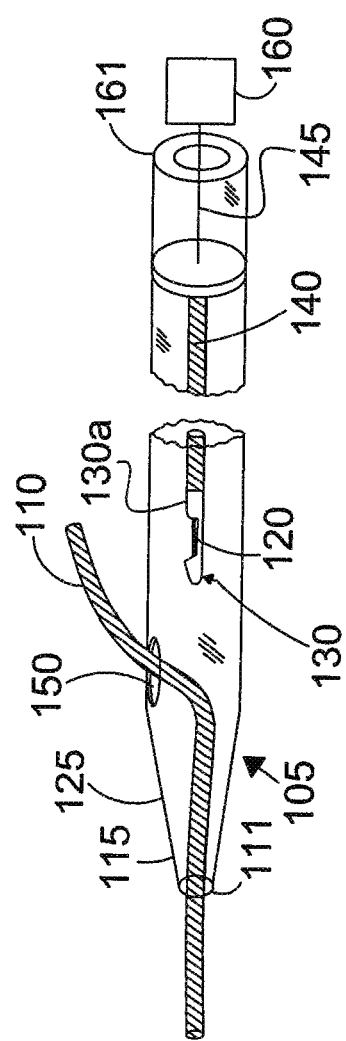
FIG. 2 is a side view of an IVUS imaging catheter, which is mechanically steered by an electric motor.

FIG. 2 is a side view of a prior art mechanically steered IVUS imaging catheter. This catheter 105 employs a RX design, whereby a guidewire 110 enters a catheter body 125 less than ~3 cm from a distal end or tip 115 of the catheter 105 in order to allow an imaging transducer 120 to be placed as close to the distal end or tip 115 as possible.

This catheter also employs a torque cable 140. The torque cable 140 is generally torsionally stiff and yet soft in flexion. The torque cable 140 is frequently made of a counter wound spring.

The ultrasonic transducer 120 is mounted in a housing 130a that allows the transducer assembly 130 to be coupled to the torque cable 140. A coaxial wire 145 carries a transmit pulse to the transducer assembly 130 and the resulting pulse echoes back to receiver processing circuits (not shown).

The guidewire 110 passes proximally into the catheter 105 through a skive 150 less than ~3 cm from the distal end 115 of the catheter 105. The guidewire 110 then exits through exit 111 at the distal end 115 of the catheter 105.

The torque cable 140 is driven by an electric motor 160. The electric motor 160 is located at a proximal end 161 of the catheter 105, and rotates the torque cable 140 at or around 1800 rpm so as to produce a stream of ultrasonic images at ~30 frames (complete ~360 degree rotation images) every second.

Such a product as discussed above has been commercially produced by Boston Scientific and Hewlett-Packard. Similar products are described in Born et al., "Early and Recent Intraluminal Ultrasound Devices," International journal of Cardiac Imaging, 4:79-88 (1989), which is hereby incorporated by reference.

FIGS. 3A and 3B are side views of prior art electronically steered IVUS catheters. FIG. 3A shows an OTW design, while FIG. 3B shows an RX design. In these catheters 205, 305, the transducer assembly 230, 330 and an electronic multiplexing circuit assembly 270, 370 have been fabricated in the shape of concentric cylinders so as to achieve a dual purpose of leaving a center of the catheter 205, 305 open for the passage of a guidewire 210, 310 and placement of the transducer assembly 230, 330 as far distally as possible. In the case of electronically steered IVUS catheters, there is no need for a torque cable extending through the center of the catheter and therefore, both the OTW design shown in FIG. 3A and the RX design shown in FIG. 3B are easily achieved.

Figure 4:
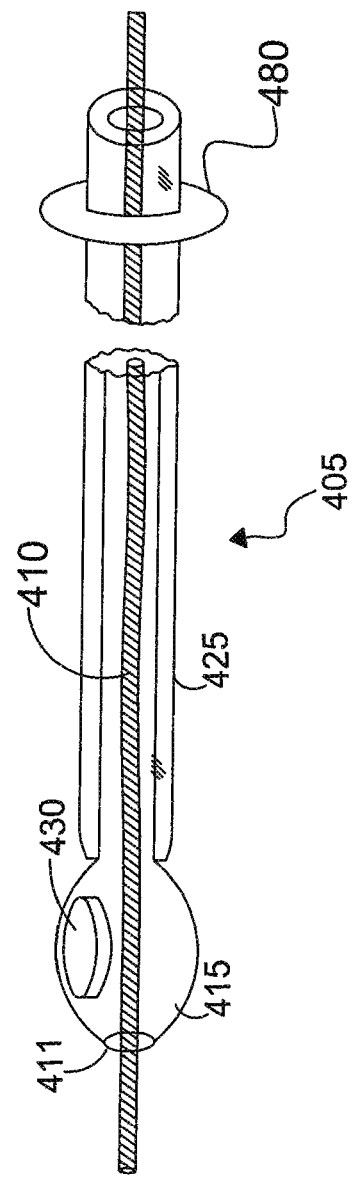
FIG. 4 is a side view of an OTW manually steered catheter.

FIG. 4 is a side view of a manually steered OTW IVUS catheter described in detail in the '141 application. The catheter 405 includes a catheter body 425, an ultrasound transducer assembly 430, and a guidewire 410. The guidewire 410 exits the catheter body 425 at exit 411. As the catheter 405 is manually rotated, an angle encoder 480 records an angular position of the catheter 405 and relays the data to imaging processing electronics (not shown) so as to associate acoustic echo information with the correct (relative) angular orientation. The entire catheter 405 is intended to be rotated to create an image; consequently, it is not easily amenable to an RX design, which would require the guidewire 410 to pass through a skive in the catheter body 425 and be rotated along with the catheter 405.

This OTW design has the advantage of allowing the placement of the transducer assembly 430 very close to the distal end 415 of the catheter 405, as in the case of the electronically steered IV US transducers shown in FIGS. 3A and 3B. However, it would be advantageous, in terms of allowing the use of shorter guidewires and more rapid exchanges of the IVUS catheter with other catheters, such as therapeutic catheters, to have an RX version of a manually steered IVUS imaging system.

Figure 5:
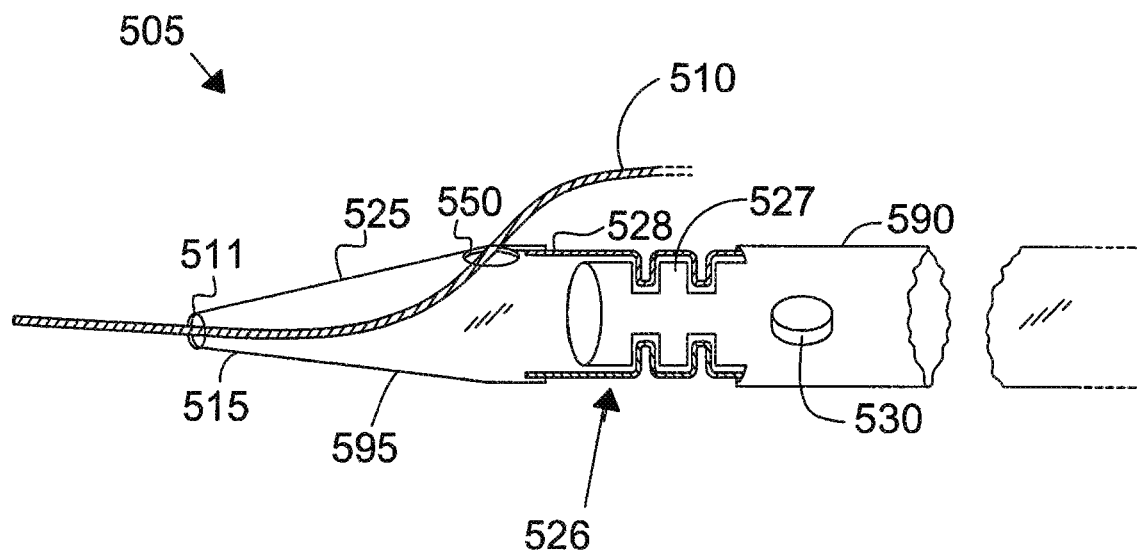
FIG. 5 is a side view of a manually steered RX design IVUS catheter according to an embodiment of the invention.

FIG. 5 is a side view of a manually steered RX design IVUS catheter according to an embodiment of the invention. This embodiment of the invention provides a manual IVUS catheter with the convenience and time efficiency of an RX design. Further, in this embodiment, a distal or RX portion 595 of the catheter 505 is relatively short so as to allow placement of the transducer assembly 530 as close to the distal most end 515 of the catheter 505 as practical. Furthermore, an imaging or proximal portion 590 of the catheter 505 is allowed to rotate freely to allow rotational steering of the transducer assembly 530, while the distal portion 595 of the catheter 505 remains stationary and provides guidewire entry or skive 550 and exit 511. A rotational bearing or joint 526 is provided between the distal or RX portion 595 and the imaging or proximal portion 590. The rotational bearing or joint 526 may meet the following criteria: extremely low friction when axially and/or flexurally loaded so as not to cause the distal end or tip 515 to rotate as the proximal portion 590 of the catheter 505 is rotated, short length and/or ability to flex so as to minimize the flexural discontinuity between the distal or RX portion 595 and the imaging or proximal portion 590 to maximize the ability of the distal or RX portion 595 to track the guidewire 510, and sufficient strength to prevent separation of the distal or RX portion 595.

The rotational bearing or joint 526 is made, in this embodiment, of a plastic on metal joint. The outer bearing member 528, which remains stationary along with the distal or RX portion 595, may be made of a material, such as HMW polyethylene. Different grades of the same material may then be used to form the distal or RX portion 595. Using different grades of the same material allows the flexural and frictional properties to be optimized and allows the materials to be heat joined by various means known in the art. Alternatively, the outer bearing member 528 may be made of a low friction material, such as Teflon, mechanically and/or adhesively bonded to the tip materials.

The inner bearing member 527, which is attached to the imaging or proximal portion 590, may be made of a highly polished metallic material, such as stainless steel. The imaging or proximal portion 590 may be constructed of materials known in the art of catheter design and manufacture, such as single or multiple durometer polymer extrusions, wire reinforced extrusions, stainless steel wire braided shafts, plain and machined hypodermic tubings, and combinations of the foregoing used to tailor the torsional and flexural properties to optimize the torque transmission and flexibility of the catheter.

Figure 6:
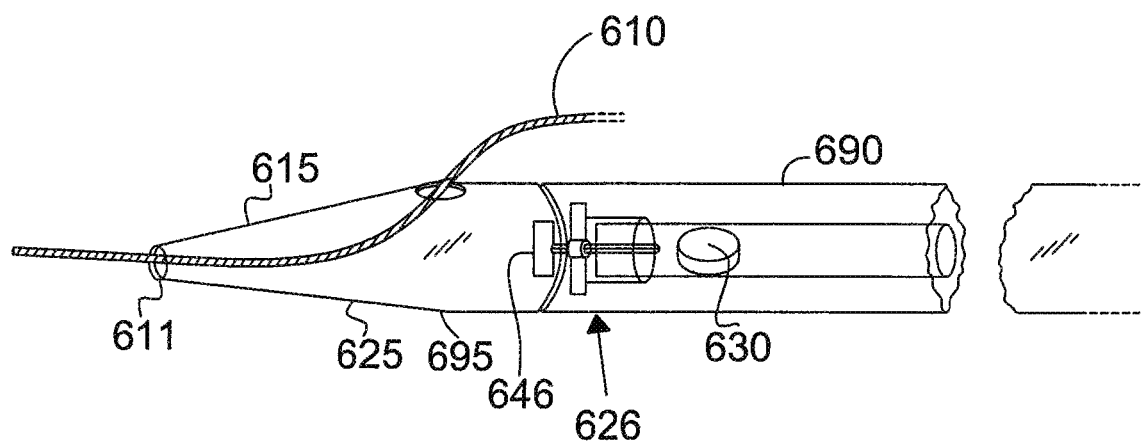
FIG. 6 is a side view of a manually steered RX design IVUS catheter according to an embodiment of the invention.

FIG. 6 is a side view of a manually steered RX IVUS catheter according to another embodiment of the invention. The embodiment of FIG. 5 is similar to the embodiment of FIG. 4 but includes a safety plug 646. The embodiment of FIG. 6 may include a rotational bearing, such as that shown in FIG. 5, in addition to the safety plug 646, or may include only the safety plug 646 to rotatably connect the distal or RX portion 695 to the imaging or proximal portion 690. Where tests have been conducted which confirm that the safety plug has sufficient tensile strength to prevent separation of the distal or RX portion 695 from the imaging or proximal portion 690, the rotational bearing may not be necessary. The embodiment shown in FIG. 6 shows the safety plug 646, which is attached, for example, by being welded or adhered, to the imaging or proximal portion 690 of the catheter 605. The safety plug 646 provides more tensile strength for preventing the distal or RX portion 695 of the catheter 605 from becoming detached from the imaging or proximate portion 690. As set forth above, the safety plug 646 may be added in addition to the rotational bearing 626 shown in FIG. 5 for added strength or can serve in place of the rotational bearing 626 shown in FIG. 5, as shown in FIG. 6.

Figure 7:
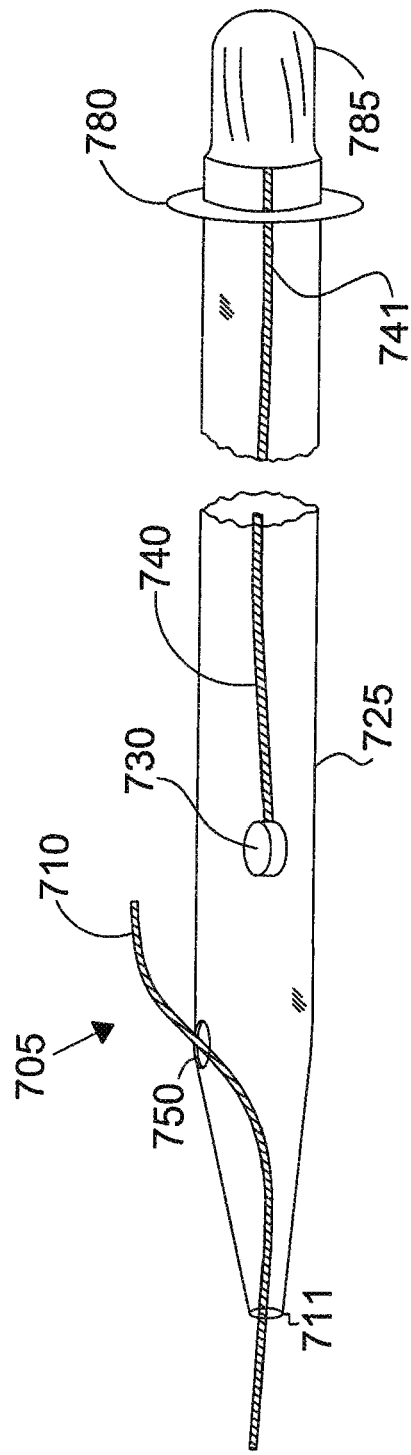
FIG. 7 is a side view of a manually steered RX design IVUS catheter according to an embodiment of the invention.

FIG. 7 is a side view of a manually steered RX catheter according to an embodiment of the invention. The catheter 705 in this embodiment allows the transducer assembly 730 to be rotated inside of a catheter body 725 by a torque cable 740 similar to the torque cable 140 used in the prior art shown in FIG. 2. At the proximal end 741 of the torque cable 740 is an angle encoder 780 that measures the angular position of the transducer assembly 730 and sends the information to imaging processing electronics (not shown) proximal to the angle encoder 780. A torquing handle 785 is provided which allows an operator to firmly grip the apparatus when rotating the torque cable 740 and transducer assembly 730.

Figure 8:
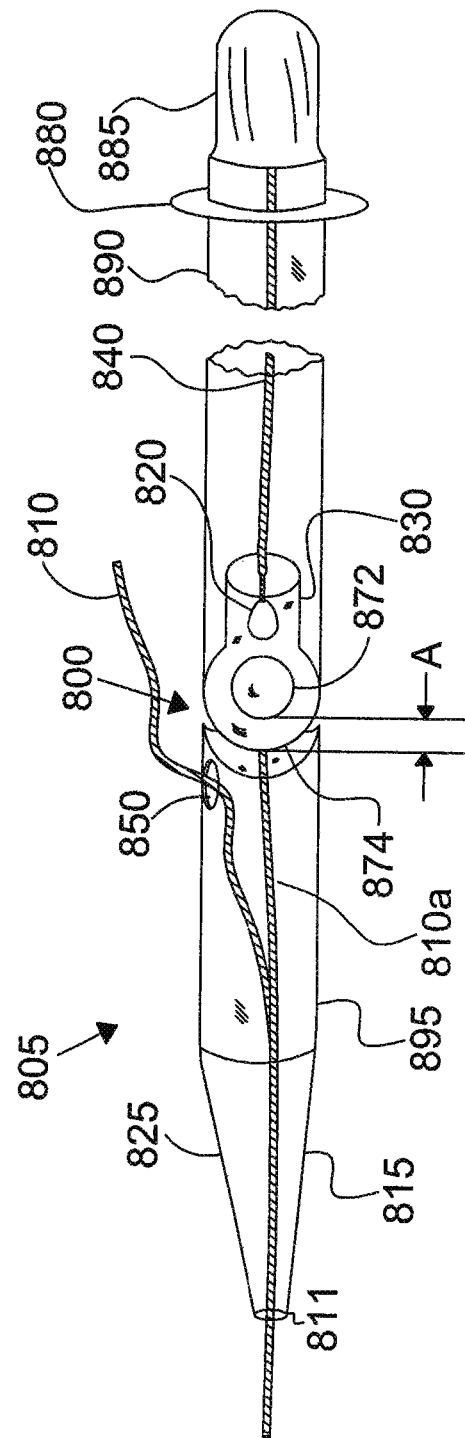
FIG. 8 is a side view of a manually steered RX design IVUS catheter according to an embodiment of the invention.

FIG. 8 is a side view of a manually steered IVUS catheter according to another embodiment of the invention. The manually steered IVUS catheter 805 of the embodiment of FIG. 8 is similar to the embodiments of FIGS. 5-7 but discloses a rotary joint 826 between the distal or RX portion 895 of the catheter 805 and the rotating imaging or proximal portion 890 of the catheter 805. In this embodiment, the rotary joint 826 comprises a ball and socket joint that connects the distal or RX portion 895 to the imaging or proximal portion 890 which holds the transducer assembly 830, including transducer 820. A ball 872, which in this embodiment is a highly polished metallic ball, is attached to a wire 810a that is joined to the distal or RX portion 895. The ball 872 is captured within a socket 874, for example, a poly-merit socket, attached to the imaging or proximal portion 890. One advantage of this embodiment is that a low rotational friction rotary joint is obtained that allows flexure at the rotary joint 826. Additionally, the wire 810a can be ground to various diameters along its length to provide a gradually varying degree of stiffness to minimize flexural discontinuities from the distal end or tip 815 through the rotational joint 826. The metallic ball 872 and wire 810a may be produced from materials, such as stainless steel and nitinol. The distance "A" between the two components 872 and 874 should be minimized to reduce the possibility of capturing or snagging tissue within the artery or on exit or retraction at the tip of the guiding catheter.

Figure 9A:
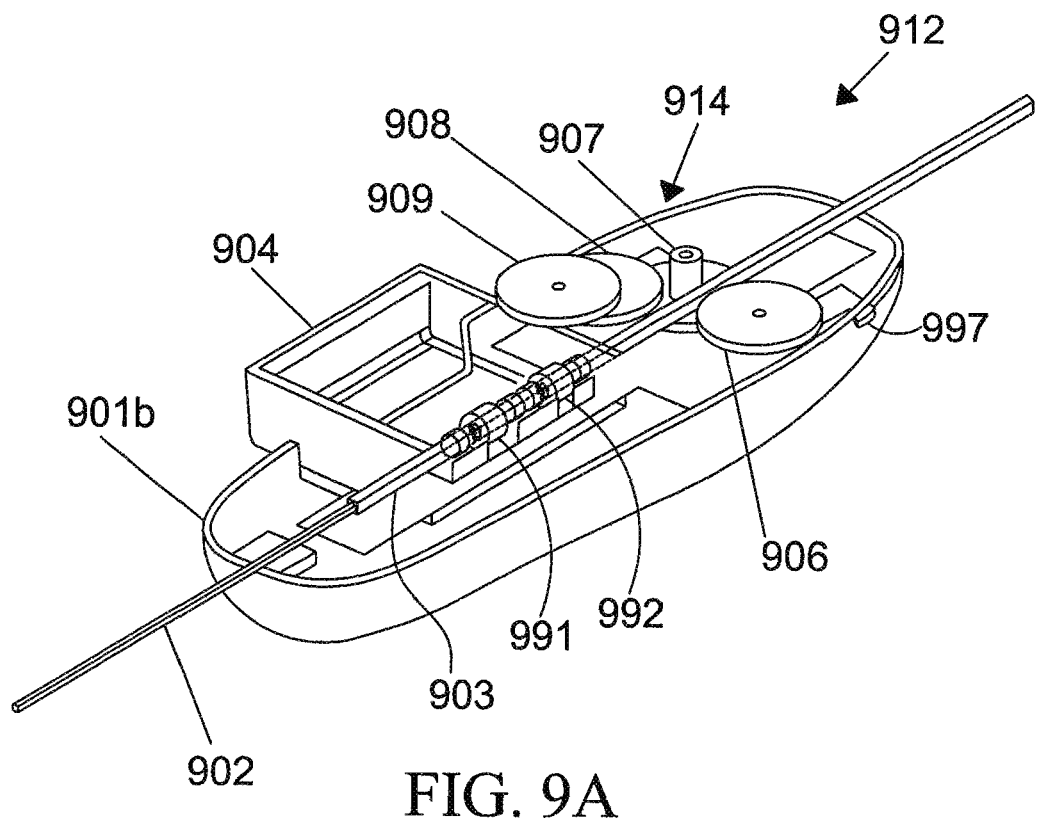
FIG. 9A is a perspective view of a handle rotation mechanism that incorporates a pullback ratcheting mechanism according to an embodiment of the invention.
Figure 9B:
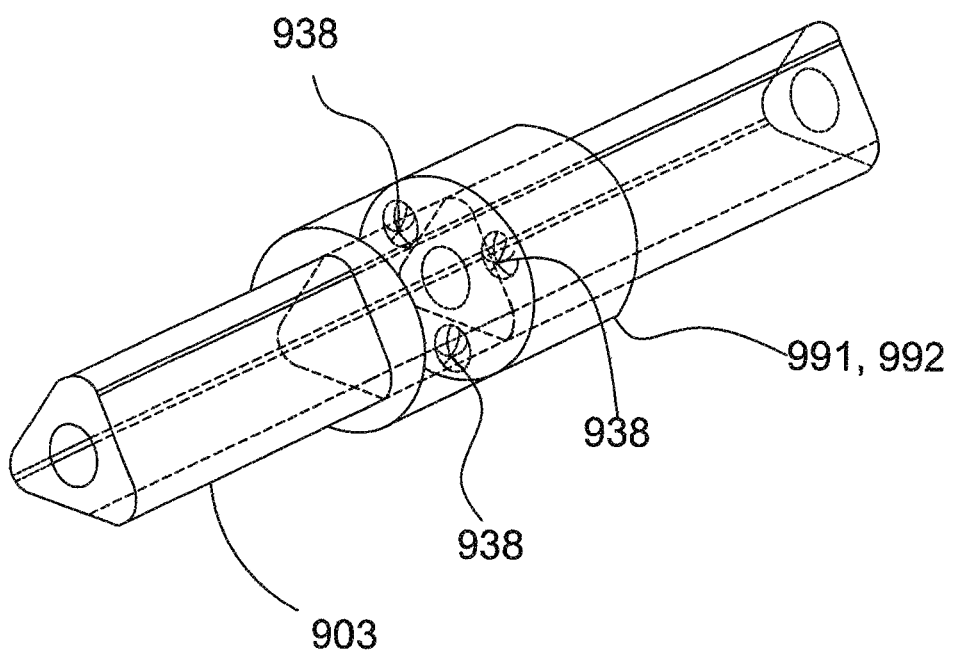
FIG. 9B is a perspective view of a drive roller mechanism contained within the pullback ratcheting apparatus of FIG. 9B.

FIGS. 9A-9D detail a handle rotation mechanism 912 for rapidly spinning a catheter one or more revolutions with each activation thereof. That is, FIG. 9A is a perspective view of a handle rotation mechanism that incorporates a pullback ratcheting mechanism according to an embodiment of the invention. FIG. 9B is a perspective view of a drive roller mechanism contained within the pullback ratcheting mechanism of FIG. 9B. FIG. 9C is a perspective view of the handle rotation mechanism of FIG. 9A, showing an upper housing portion in place. FIG. 9D is a perspective view of the handle rotation mechanism of FIG. 9A, showing an angle encoder.

The handle rotation mechanism 912 may include an angle encoder 996, as shown in FIG. 9D. Each successive activation of the handle rotation mechanism 912 can reverse the direction of rotation of a catheter so as to prevent the electrical wires (not shown) of the catheter from winding up. In addition, the handle rotation mechanism 912 can be configured to perform a pull back ratcheting operation or imaging sequence. That is, each activation of the handle rotation mechanism 912 may not only rotate the catheter, for example, ~360 degrees, but may also pull the catheter a fixed distance, for example ~0.5 mm, along a longitudinal axis of the catheter.

The handle rotation mechanism 912 may be a one person, one hand operated mechanism, which may be attached to a proximal end of a catheter. It may be permanently attached or configured as a separate piece that is attached to the catheter just prior to or during a procedure. In one embodiment, the handle rotation mechanism 912 is an integral part of the catheter so that an interventionalist or operator does not have to assemble the system prior to use. One advantage of this embodiment is that it provides a simple, low cost mechanism that is disposable after a single use. The handle rotation mechanism 912 includes a handle body 901a, 901b, which is attached to an outer sheath or catheter body 902 of a catheter. A rotating shaft 903 is attached to a rotation/translation mechanism within the handle rotation mechanism 912. The rotating shaft 903 is attached to the catheter body 902 by means of shaft position fitting 998.

A fluid injection port 993a, as shown in FIGS. 9C-9D, may be supplied at a junction of the catheter body 902 to the handle body 901 so that the space inside the catheter body 902 can be flushed initially and periodically with, for example, heparinized saline, to initially prevent air embolization and later prevent blood from filling the space and compromising the materials' frictional and imaging properties.

The catheter body 902 may be a single lumen polymer extrusion, for example, made of polyethylene (PE), although other polymers may be used. Further, the catheter body 902 may be formed of multiple grades of PE, for example, HDPE and LDPE, such that the proximal portion exhibits a higher degree of stiffness relative to the mid and distal portions of the catheter body. This configuration provides an operator with catheter handling properties required to efficiently perform the desired procedures. Additionally, the catheter body may be approximately 110 cm in length.

In this embodiment, squeezing a handle lever 904 causes the shaft 903 to rotate, for example, ~360 in one direction. A subsequent squeeze of the handle lever 904 causes the shaft 903 to rotate, for example, ~360 in the opposite direction. The ~360 degree rotation is given by way of example, as other degrees of rotation may be appropriate based on the particular application. For example, different shaft stiffness and configurations for coronary and peripheral vascular system usage may require the rotation mechanism to turn the shaft further than ~360 degrees to achieve ~360 degrees of rotation at the distal end of the catheter in-vivo.

The rotational motion of the shaft 903 is caused by the lever 904 contacting a rotational first drive roller 991. As the lever 904 is moved towards a centerline of the shaft 903 an inner surface of the lever 904 bears against the first drive roller 991. The drive roller 991 may have a round, square, or other cross-section and may be made from an elastomer or other material that provides a high degree of friction against the lever 904. When the lever 904 reaches the end of its travel, a trip mechanism (not shown) causes the lever 904 to shift position. The shift in position causes the lever 904 to contact a rotational second drive roller 992. Releasing the lever 904 to its extended position causes the second drive roller 992 to freely rotate due to a clutch mechanism (not shown) within. The next push of the lever 904 causes the second drive roller 992 to rotate the shaft 903 in a direction opposite the first drive roller 991. This process is repeated upon each press of the lever 904. The stroke of the lever 904 and the diameter of the drive rollers 991, 992 may be chosen to accomplish the ~360 degree rotation. As previously discussed, it may be advantageous to rotate the shaft 903 further than ~360 degrees or multiple times for imaging purposes. In such a case, the lever travel to roller diameter may be selected to achieve the desired rotation.

FIG. 9B discloses elements of the translation mechanism 914 of the handle rotation mechanism 912 of FIG. 9A. That is, the drive rollers 991, 992 may have an inner geometric cross-section, such as a triangle. The shaft 903 of the catheter contained within the handle rotation mechanism 912 may have a corresponding cross section sized to provide clearance within the roller 991, 992. This configuration allows the rollers 991, 992 to drive the shaft 903 yet still allows for translational movement. As shown, steel balls 938 may be included to reduce the frictional properties of the shaft 903 sliding within the drive rollers 991, 992.

The shaft 903 attaches to the handle rotation mechanism 912 using the shaft position fitting 998, as discussed above and shown in FIGS. 9C-9D, which allows a relative axial position of the shaft 903 versus the catheter body 902 to be adjusted within a designed limit. The shaft position fitting may be a plastic or metal collar or adjustable gasket that can be tightened sufficiently to grip the shaft 903.

A switch 997, as shown in FIGS. 9A, 9C, and 9D, is provided on the handle rotation mechanism 912 to change the mode of operation between rotation only and rotation with translation (pullback). The translation mechanism 914 causes a translation pinch roller 906 to bear on a surface of the shaft 903 and thereby sandwich it between the translation pinch roller 906 and a translation drive roller 907. The translation drive roller 907 is driven by rollers 908, 909, which in turn are driven by the lever 904. By selecting and arranging different diameter rollers, a ratio of lever movement to catheter translation may be designed. Further, the various rollers may be molded plastic with overmolded elastomeric frictional surfaces.

The handle rotation mechanism 912 may incorporate an angular position sensor 996, as shown in FIG. 9D, to provide catheter shaft rotational data to the ultrasound system. The angular position sensor 996 may be configured to directly read the angular rotation via an encoder wheel 996a attached to the catheter shaft 903 and optical encoder 996b positioned adjacent thereto, as shown in FIG. 9D, or indirectly via sensing the movement of the handle lever 904.

The foregoing describes a handle rotation mechanism configured to rotate a catheter in one direction directly followed by rotation in the opposite direction. However, it may be desirable to provide a mechanism that allows repeated rotations in a particular direction. In this instance, the handle rotation mechanism may contain a clutch mechanism that allows the handle rotation mechanism to return to its start position, thereby allowing for multiple actuations in the same direction. Further, a switch may be provided to change the direction of rotation. Allowance for windup of the catheter electrical connection may be provided by swivel connectors, such as a slip ring or inductive rotary electrical couplers.

The above described invention is directed to various embodiments of a catheter that permit an RX design to be used for a manually steered IVUS catheter. Such catheters, and their associated imaging systems, have significant cost advantages over both mechanically steered, motor driven IVUS systems and electronically steered IVUS systems.

An additional advantage of the invention deals with reduction of motion artifacts that can occur with a manually steered IVUS system. For example, since the heart is constantly beating, and most vessels of interest have an open lumen diameter that is significantly larger than the diameter of the catheter, a manually rotated catheter can suffer from motion artifact. For example, if a complete ~360 scan of an artery takes ~2 seconds to sweep out and in that ~2 seconds, 2 or 3 heart beats occur, the relative motion of the catheter in the open lumen can create severe artifacts in the image. This is a consequence of the fact that the position of the ultrasonic transducer relative to the vessel is changing while the image is being swept out. By employing a hand activated mechanism that automatically spins the catheter ~360 degrees in less than an ~half second, the artifact can be removed or substantially reduced.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A catheter comprising:
   a catheter body configured for introduction into an area of interest within a patient's body, the catheter body comprising a distal portion and a proximal portion, the proximal portion comprising a first lumen along a length of the proximal portion but not extending into the distal portion, the distal portion comprising a second lumen along a length of the distal portion but not extending into the proximal portion;
   a joint coupling the distal portion and the proximal portion of the catheter body; and
   a manual steering device coupled to the catheter body, wherein actuation of the manual steering device translates the proximal portion of the catheter body without translating the distal portion of the catheter body.

2. The catheter of claim 1, wherein the catheter further comprises a device for imaging, diagnosing and/or treating an area of interest.

3. The catheter of claim 2, wherein the imaging, diagnosing and/or treating device is disposed within the first lumen of the catheter body.

4. The catheter of claim 2, wherein the imaging, diagnosing and/or treating device comprises an ultrasound transducer.

5. The catheter of claim 1, wherein the second lumen extends from entry and exit ports disposed on the distal portion.

6. The catheter of claim 5, wherein the second lumen is configured to receive a guidewire.

7. The catheter of claim 1, wherein the joint comprises a rotational bearing.

8. The catheter of claim 7, wherein the proximal portion is configured to rotate with respect to the distal portion.

9. The catheter of claim 7, wherein the rotational bearing comprises an outer bearing member attached to the first stationary distal end portion and an inner bearing member attached to the second rotatable portion.

10. A method of using a catheter to image, diagnose and/or treat an area of interest in a patient's body, comprising:
    introducing a guidewire into an area of interest in a patient's body;
    loading a catheter for imaging, diagnosing and/or treating onto the guidewire, the catheter comprising a catheter body configured for introduction into an area of interest within a patient's body, the catheter body comprising a distal portion and a proximal portion, the proximal portion comprising a first lumen along a length of the proximal portion but not extending into the distal portion, the distal portion comprising a second lumen along a length of the distal portion but not extending into the proximal portion, the distal portion and the proximal portion of the catheter body coupled by a joint, wherein the loading includes positioning the guidewire in the second lumen;
    advancing the catheter to an area of interest; and
    manually steering the catheter to image, diagnose, and/or treat the area of interest, wherein the manually steering the catheter includes translating the proximal portion of the catheter body via a manual steering device coupled to the catheter body without translating the distal portion of the catheter body.

* * * * *